(12) United States Patent
Lambert et al.

(10) Patent No.: US 7,834,172 B2
(45) Date of Patent: Nov. 16, 2010

(54) COMPOSITION COMPRISING AT LEAST ONE NUCLEOSIDIC MOIETY AS A THERAPEUTIC AGENT, AND CKC

(75) Inventors: Gregory Lambert, Chatenay Malabry (FR); Frederic Lallemand, Fresnes (FR)

(73) Assignee: Novagali Pharma SA, Evry (FR)

( * ) Notice: Subject to any disclaimer, the term of this patent is extended or adjusted under 35 U.S.C. 154(b) by 171 days.

(21) Appl. No.: 11/939,840

(22) Filed: Nov. 14, 2007

(65) Prior Publication Data

US 2009/0124565 A1  May 14, 2009

(51) Int. Cl.
*C07H 21/04* (2006.01)
*A61K 31/70* (2006.01)

(52) U.S. Cl. ......................... 536/24.5; 514/44
(58) Field of Classification Search ........................ None
See application file for complete search history.

(56) References Cited

U.S. PATENT DOCUMENTS

| 7,169,411 B1 * | 1/2007 | Kabanov et al. ............. 424/486 |
| 2003/0040497 A1 * | 2/2003 | Teng et al. ..................... 514/44 |
| 2005/0025833 A1 * | 2/2005 | Aschkenasy et al. ......... 424/484 |
| 2006/0100288 A1 * | 5/2006 | Bague et al. ................. 514/642 |

OTHER PUBLICATIONS

Lambert, G. "Polyalkylcyanoacrylate Nanospheres and Nanocapsules for the Delivery of Antisense Oligonucleotides", *Journal of Dispersion Science and Technology*. vol. 24, Nos. 3 and 4, pp. 439-252, 2003.

* cited by examiner

*Primary Examiner*—Tracy Vivlemore
(74) *Attorney, Agent, or Firm*—Young & Thompson

(57) ABSTRACT

Composition comprising at least one nucleosidic moiety and cetalkonium chloride and pharmaceutical use thereof for prevention, treatment or relief of eye, lung, and/or respiratory tract conditions.

18 Claims, 2 Drawing Sheets

Figure 1:
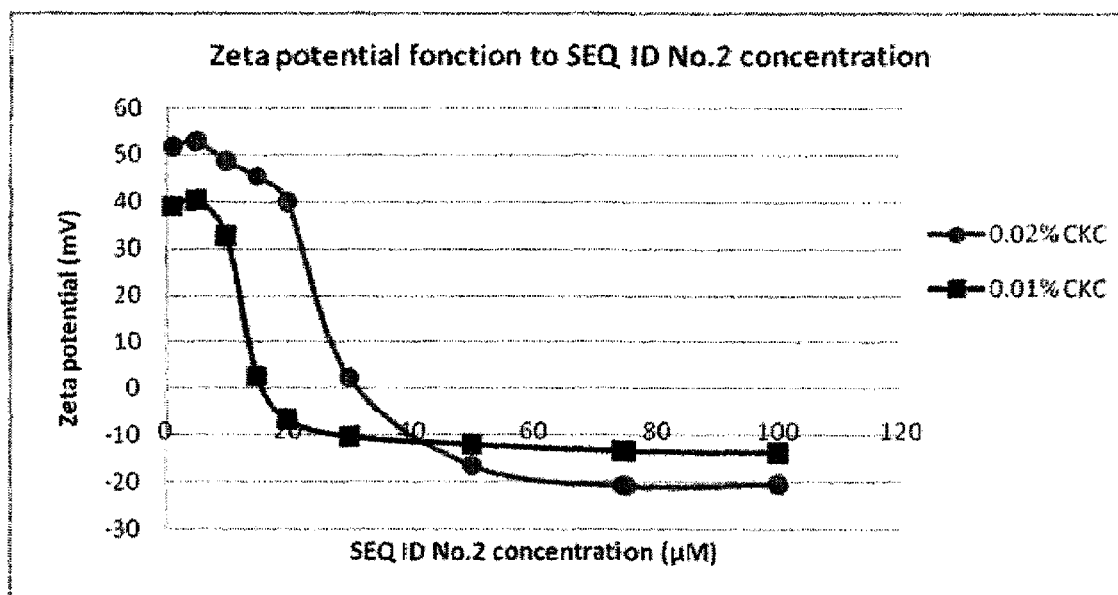

COMPOSITION COMPRISING AT LEAST ONE NUCLEOSIDIC MOIETY AS A THERAPEUTIC AGENT, AND CKC

This invention relates to the prevention, treatment or relief of eye, lung and/or respiratory tract conditions. More precisely, this invention is directed to the use of at least one nucleosidic moiety as a therapeutic agent, in a composition further comprising CKC.

Some nucleosidic moieties are now well-recognized as therapeutic agents. To date, nucleic acid-based therapeutics have generally been delivered by injection, subcutaneously, intravenously or intravitreally. However, as these routes of administration are not optimal, searches on topical administration of nucleic acids were conducted: for example US2005238606 describes a composition for delivery of a nucleic acid to a hair follicle comprising a nucleic acid and an aqueous solution; WO9960012 describes a pharmaceutical emulsion comprising at least one oligonucleotide and a penetration enhancer, such as fatty acids, bile salts, chelating agents, capable to enhance the stability of oligonucleotides and other nucleic acids and/or their transport across cell walls and/or into cells. In J. of Dispersion Science and Technology, Vol. 24, Nos 3&4, pp. 439-452, 2003, Gregory Lambert addresses the low chemical stability of antisense oligonucleotides and their absorption onto the surface of nanospheres or within nanocapsules However, administration of oligonucleotides to their site of action still remains a challenge. For a satisfactory delivery of oligonucleotides in the eye, in the lungs or in the nasal and/or respiratory tracts, it is sought a way of administration where oligonucleotides remain on the site of administration, without being washed out by body fluids or degraded, and are safely transported across cell walls and/or into cells.

The administration of therapeutic nucleosidic moieties as therapeutic agents for the treatment of eye, lung and/or respiratory tract conditions have not much been addressed, and there still is a need for well-accepted and not toxic new formulations enhancing stability and/or improving penetration of said nucleosidic moieties within the targeted cells.

The Applicant has noticed that cationic surfactants may have a role in stabilizing nucleosidic moieties, and made a number of attempts using various quaternary ammonium compounds. When selecting CKC a very specific quaternary ammonium compound, the Applicant observed unexpected results: he noticed that the stability of the nucleosidic moiety in time may be enhanced; CKC may also have an action in enhancing the transport of oligonucleotides across mucosal membranes and/or into the cells, especially but not limitatively, when used in solutions or emulsions. CKC was selected both for its complexation abilities, especially its ability of complexing oligonucleotides and for its cationic power and its lack of toxicity.

Thus, in a first aspect, the present invention relates to the use of CKC to enhance stability and improve penetration of nucleosidic moieties within target cells. Without wanting to be linked by a theory, the Applicant considers that the positive charge of CKC may act as stabilizer of the nucleosidic moiety. Therefore, the amount of CKC in the compositions of the invention may be dependent on the length of the nucleosidic moiety. In a preferred embodiment, the ratio CKC/negative charge is below 0.55. On another embodiment, the nucleosidic moiety is an oligonucleotide, and the ratio CKC/number of mers of the oligonucleotide is below 0.55, preferably from 0.001 to 0.5.

On another embodiment, the composition of the invention comprises from 0.001 to 0.05% w/w of CKC, preferably from 0.005 to 0.04% w/w of CKC and more preferably 0.08 to 0.03% w/w of CKC.

In a second aspect, the invention relates to a composition comprising at least one nucleosidic moiety, preferably an oligonucleotide, and a specific cationic agent, which is a cetalkonium halide, preferably CKC. The nucleosidic moiety preferably is a bioactive molecule. Preferably, the nucleosidic moiety is a therapeutic molecule, and is provided in the composition in an amount sufficient for therapeutic effect.

In a third aspect, the present invention provides a medicament comprising an effective amount of at least one nucleosidic moiety such as a nucleoside, a nucleotide, or a nucleic acid, and cetalkonium chloride.

In a fourth aspect, the present invention provides pharmaceutical compositions comprising an effective amount of at least one nucleosidic moiety such as a nucleoside, a nucleotide, or a nucleic acid, and cetalkonium chloride, in combination with one or more pharmaceutically acceptable excipients.

The nucleosidic moiety may be a ribozyme, a peptide nucleic acid (PNA), or an aptamer, but preferably is an oligonucleotide.

The term "effective amount" as used herein refers to an amount sufficient to cause a beneficial or desired clinical result (e.g. improvement in clinical condition).

The term "oligonucleotide" as used herein refers to a single stranded or double stranded sequence of nucleic acids, more preferably of ribonucleic acid (RNA) or deoxyribonucleic acid (DNA) or mimetics thereof; said nucleic acids may be sens or antisens. According to an embodiment of the invention, an oligonucleotide includes 5 to 50 nucleotides, more preferably 9 to 30 nucleotides and even more preferably from 13 to 25 nucleotides. According to an embodiment, the molecular weight of the oligonucleotide of the invention ranges from 500 to 15000 Daltons, more preferably, 4000 to 8000 Daltons. According to the invention, the term "oligonucleotide" non-limitatively includes double stranded nucleic acids known as short interfering RNAs (siRNAs), generally comprising 12 to 40 nucleotides; according to the invention, the term "oligonucleotide" non-limitatively includes DNA- or RNA-aptamers; according to the invention, the term "oligonucleotide" includes oligonucleotides which have been modified to increase their stability and/or affinity for their target; according to the invention, the term "oligonucleotide" non-limitatively includes any natural DNA or RNA which has been modified to enhance its properties or its stability. The term "oligonucleotide" in the meaning of this invention, excludes polynucleotides. The term "oligonucleotide" in the meaning of this invention, also includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

As CKC in the meaning of this invention, is meant cetalkonium chloride (CAS122-18-9).

According to an embodiment, the composition is an emulsion. Preferably, the composition of the invention is a submicronic oil-in-water emulsion comprising at least one nucleosidic moiety and CKC. In this embodiment, preferably, the oil is selected among MCT, castor oil, corn oil, soybean oil, olive oil, mineral oil, safflower oil; MCT is most preferred; preferably also, the emulsion includes at least one surfactant, preferably selected from tyloxapol, polysorbate 80, montane 20, poloxamer, cremophor and/or lecithins. Preferably, polysorbate 80 or tyloxapol the amount of surfactant ranges between 0 and 5% in weight to the total weight of the composition; Preferably, the droplet size ranges between 50 nm and 500 nm, preferably between 100 and 400 nm, more preferably between 150 and 250 nm measured with High performance particle sizer (HPPS), Malvern, UK. According to an embodiment, the emulsion includes only one surfactant. Preferred surfactants for the emulsions of the invention are poloxamer, tyloxapol and polysorbate 80. Preferably, the emulsion includes MCT, polysorbate 80 and propylene glycol.

According to an embodiment, the oligonucleotide includes 5 to 50 nucleotides, more preferably 9 to 30 nucleotides and even more preferably from 13 to 25 nucleotides.

According an embodiment, the oligonucleotide is a modified nucleic acid. According an embodiment, the oligonucleotide is a short interfering RNA.

According to another embodiment, the oligonucleotide is an antisense oligonucleotide directed against specific cellular receptors in order to inhibit general inflammation, including inflammation associated with asthma and allergy.

According to a preferred embodiment, the oligonucleotide has the following 5'-3' sequence:

```
TGG CAC TTT AGG TGG CTG     (SEQ ID No. 1)
```

According to another preferred embodiment, the oligonucleotide has the following 5'-3' sequence

```
ACT CAT ATT CAT AGG GTG.    (SEQ ID No. 2)
```

In an embodiment of the invention, the composition includes at least one particle, nanoparticle, sphere, nanosphere, capsule or nanocapsule, liposome, niosome, oleosome and the nucleosidic moiety is associated in the composition with said particle.

In another embodiment, the composition is a colloidal system including emulsions, micelles, inverted micelles, block or non-block polymer micelles and the nucleosidic moiety is within or adsorbed at the surface of said colloidal system.

According to a preferred embodiment, the composition is an emulsion, more preferably an oil-in-water emulsion. In this embodiment, the oligonucleotide is adsorbed at the surface of the oil phase. According to a first embodiment, the emulsion is a cationic emulsion. According to a second embodiment, the emulsion is an anionic emulsion.

The composition of the invention is preferably dedicated to the prevention, treatment or relief of eye, lung, and/or respiratory tract conditions. According to an embodiment, said conditions include allergy and asthma, eye conditions such as eye allergies, eye inflammation, dry eye conditions, red eyes, VKC, diseases of the posterior segment of the eye such as diabetic retinopathy and macular degeneration.

According to another embodiment, the composition of the invention includes an oligonucleotide alone or in combination with another therapeutic agent, including other oligonucleotides.

According to an embodiment, the composition does not include any other cationic agents but CKC.

According to another embodiment, the composition includes an anionic surfactant. Preferred anionic surfactants are lecithins.

According to another embodiment, the composition of the invention is to be administered directly or otherwise, to all or a portion of the alimentary canal, skin, such as for example dermis or epidermis, eyes, pulmonary tract, respiratory tract, such as for example nose and/or throat, or to the mucosa, such as for example urethra or vagina of an animal, including a human. Preferably, the composition of the invention is administered topically, or by spray or inhalation.

An advantage of the invention is that the composition may be for local administration and the Applicant notices that direct and local administrations may optimize product efficacy because application is on target site or proxi to the target site. Unexpectedly, the association of a nucleosidic moiety with CKC seems to lead to a significant improvement for penetrating the nucleosidic moiety into target cells.

According to another embodiment, the composition is an ophthalmic composition. Preferably, the composition is a submicron oil-in-water ophthalmic emulsion. In this embodiment, the amount of nucleosidic moiety preferably ranges between 0.001 and 0.1% w/w, preferably between 0.01 and 0.05 w/w of the total composition.

According to another embodiment, the composition is a composition for the lungs and respiratory tracts. Preferably, the composition is a submicron oil-in-water ophthalmic emulsion. In this embodiment, the amount of nucleosidic moiety preferably ranges between 0.001 and 1.0 preferably between 0.05 and 0.5 w/w of the total composition.

This invention also relates to a process for the preparation of a composition of the invention, wherein a composition, preferably an oil-in-water emulsion, free of active agent is prepared, and the oligonucleotide is then incorporated within said emulsion. According to an embodiment, the invention also relates to a composition and process of preparing the same, wherein a composition, preferably an oil-in-water emulsion, containing at least one active agent which is not an oligonucleotide is prepared, and the oligonucleotide is then incorporated within said emulsion This invention also relates to a kit comprising two containers, a first container comprising a composition, preferably an oil-in-water emulsion including CKC, and a second container comprising the oligonucleotide. According to an embodiment, the oligonucleotide present in said container is in powder form. Advantageously, the oligonucleotide present in said container is lyophilized.

This invention also relates to a process of preparation of an oil-in-water emulsion containing an oligonucleotide, where the oligonucleotide is mixed to the emulsion containing CKC, prior to use.

This invention will now be illustrated by the following non-limiting examples, which shall be read together with FIGS. 1 and 2.

FIG. 1 refers to Example 1 and represents the zeta potential of the emulsions at various concentration of oligonucleotide.

Figure 2:
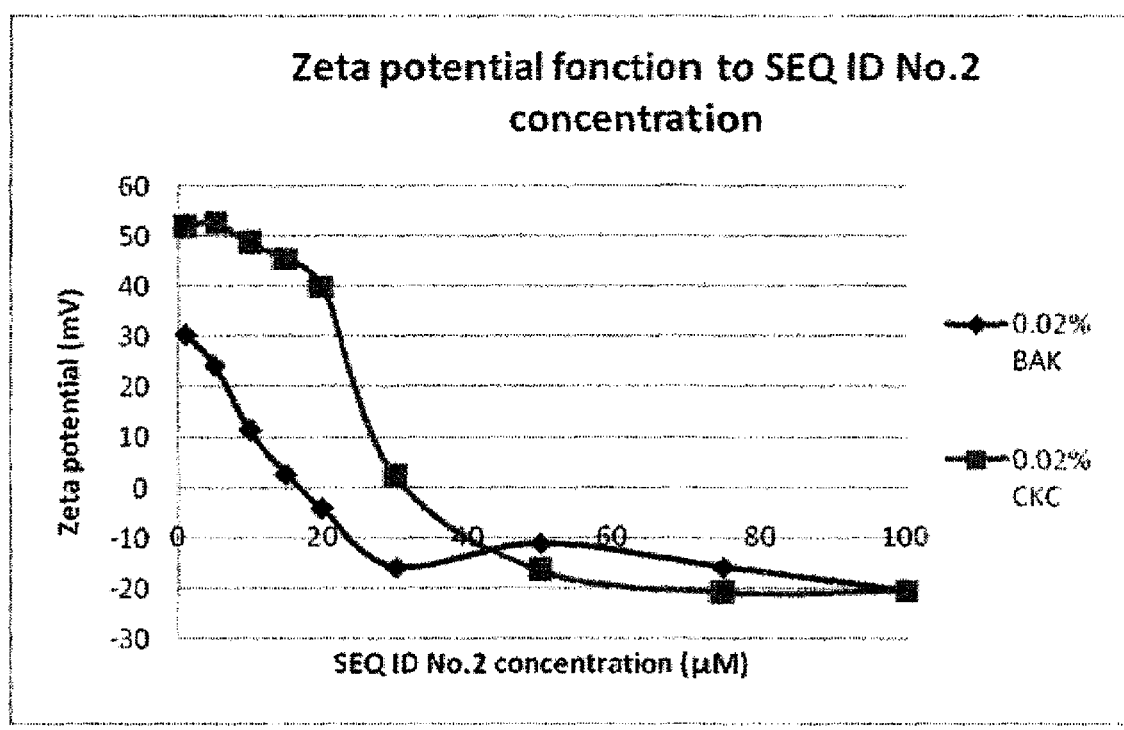

FIG. 2 refers to Example 4 and is a comparison between emulsions comprising CKC, according to the invention, versus emulsions containing BAK;

The present invention also includes a sequence listing for SEQ ID No.1 and SEQ ID No.2.

EXAMPLE 1
Preparation of Two Cationic Emulsions and Association with Increasing Oligonucleotide Concentrations Various emulsions according to the invention were prepared. These emulsions include the following ingredients and an oligonucleotide is added to the aqueous phase.

Cationic Emulsions with CKC:

|  | Products | Emulsion 1 | Emulsion 2 |
|---|---|---|---|
| Oily phase | Medium chain triglycerides | 4 | 4 |
| aqueous phase | CKC | 0.02 | 0.01 |
|  | Polysorbate 80 | 0.6 | 0.6 |
|  | Propylene glycol | 2.00 | 2.00 |
|  | Water | 93.38 | 93.39 |

Different quantities of a 18 mer-phosphorotioate oligonucleotide (for example SEQ ID No.2) solution are added to the emulsions. Zeta potential is measured after each addition. The FIG. 1 represents the zeta potential of the emulsions at various concentration of the oligonucleotide having SEQ ID No.2 sequence in the emulsions. With 0.02% of CKC in the emulsion, the emulsion charge is inverted from positive to negative at concentrations of SEQ ID No.2 over 30 µM. With 0.01% CKC, the charge inversion occurs with about 15 µM of the oligonucleotide having the SEQ ID No.2 sequence. Emulsions with zeta potential absolute values above 10 mV are considered to be physically stable; moreover, the positive zeta potential is responsible for an increased penetration in biological membranes and/or cells.

EXAMPLE 2
Preparation of a Cationic Emulsion

A cationic emulsion according to the invention, including 0.015% 18-mer oligonucleotide SEQ ID No.2 (26 µM) was prepared.

|  | Products | Cationic emulsion % w/w |
|---|---|---|
| Oily phase | Medium chain triglycerides | 4 |
| aqueous phase | CKC | 0.02 |
|  | Polysorbate 80 | 0.60 |
|  | Propylene glycol | 2.00 |
|  | SEQ ID No. 2 | 0.015 |
|  | Water | 93.365 |

This cationic emulsion has a zeta potential of +20 mV. With a zeta potential of +20 mV, this emulsion is physically stable; moreover, the positive zeta potential is responsible for an increased penetration in biological membranes and/or cells.

EXAMPLE 3

Preparation of an Anionic Emulsion

An anionic emulsion according to the invention, including 0.04% of a 18 mer-phosphorotioate oligonucleotide (SEQ ID No.2) (70 µM) was prepared.

|  | Products | Cationic emulsion % w/w |
|---|---|---|
| Oily phase | Medium chain triglycerides | 4 |
| aqueous phase | CKC | 0.02 |
|  | Polysorbate 80 | 0.60 |
|  | Propylene glycol | 2.00 |
|  | SEQ ID No. 2 solution | 0.04 |
|  | Water | 93.34 |

This anionic emulsion has a zeta potential of −15 mV. With a zeta potential of −15 mV, this emulsion is physically stable; the advantage of this emulsion is the high oligonucleotide concentration which will compensate a sub-optimal penetration due to the negative zeta potential.

EXAMPLE 4
Comparative Example
Cationic Emulsions with CKC and BAK

|  | Products | Emulsion 1 | Emulsion 3 |
|---|---|---|---|
| Oily phase | Medium chain triglycerides | 4 | 4 |
| aqueous phase | BAK |  | 0.02 |
|  | CKC | 0.02 |  |
|  | Polysorbate 80 | 0.60 | 0.60 |
|  | PG | 2.00 | 2.00 |
|  | Water | 93.38 | 93.38 |

If CKC is replaced by another cationic agent such as BAK (benzalkonium chloride, FeF Chemicals, Denmark) at the same concentration (0.02%) the emulsion becomes negative at 20 µM. CKC is needed to ensure a positive charge at high concentration of 18 mer-phosphorotioate oligonucleotide (SEQ ID No.2). The CKC, due to its higher lipophilicity compared to BAK is more associated to the emulsion surface, resulting in an improved oligonucleotide binding potential.

EXAMPLE 5
CKC/Oligonucleotides Complexes with CKC

CKC/Oligonucleotides complexes are formed due to the interaction of the CKC positive charges with the oligonucleotides negative charges conferred by each of the bases (18 in the case of SEQ ID No.2). The complex formation has the effect of neutralizing part of the negative charges of the oligonucleotides and to bring some lipophilic moieties to the complex. A stable complex with a balanced lipophilicity enhances the oligonucleotide penetration in the cells due to the affinity with the lipophilic cell membranes.

This table shows that with high CKC content, the formed complexes precipitates due the hydrophobic attraction between the CKC lipophilic tails. Stable complexes are formed without precipitation at ratios below 10/18 (CKC/oligonucleotide negative charges, the few lipophilic moieties being unable to induce the precipitation.

| ratio CKC/negative charges | CKC µM | SEQ ID No. 2 solution µM | Observation |
|---|---|---|---|
| 55.55 | 10000 | 10 | ↓↓↓ precipitation |
| 5.55 | 1000 | 10 | ↓↓↓ precipitation |
| 4.17 | 750 | 10 | ↓↓ precipitation |
| 2.77 | 500 | 10 | ↓ precipitation |
| 2.22 | 400 | 10 | ↓ precipitation |
| 1.66 | 300 | 10 | ↓ precipitation |
| 1.11 | 200 | 10 | ↓ precipitation |
| 0.83 | 150 | 10 | ↓ precipitation |
| 0.55 | 100 | 10 | No precipitation |
| 0.27 | 50 | 10 | No precipitation |
| 0.05 | 10 | 10 | No precipitation |

In conclusion, we identified optimal CKC/oligonucleotide charge ratios at 0.55 or below leading to stable, unprecipitated complexes.

The invention claimed is:

1. A composition comprising at least one oligonucleotide and cetalkonium chloride (CKC), wherein the ratio of CKC to mers of the oligonucleotide is below 0.55.

2. The composition according to claim 1, wherein the oligonucleotide comprises 5 to 50 nucleotides.

3. The composition according to claim 1, wherein the oligonucleotide is a short interfering RNA.

4. The composition according to claim 1, further comprising at least one other therapeutic agent.

5. The composition according to claim 1, wherein the oligonucleotide is within a colloidal system comprising emulsions, micelles, inverted micelles, or block or non-block polymer micelles.

6. The composition according to claim 1, wherein the oligonucleotide is associated in the composition with at least one of a particle, nanoparticle, sphere, nanosphere, capsule or nanocapsule, liposomes, niosomes, or oleosomes.

7. The composition according to claim 1, wherein the composition is in the form of a submicronic oil-in-water emulsion comprising an oil, and at least one surfactant.

8. The composition according to claim 7, wherein the surfactant is selected from tyloxapol, polysorbate 80, montane 20, poloxamer, cremophor and/or lecithins.

9. The composition according to claim 7, wherein the amount of surfactant in the composition is in a range from 0.001% to 5% by weight to the total weight of the composition.

10. The composition according to claim 7, wherein the oil-in-water emulsion comprises only one surfactant.

11. The composition according to claim 1, wherein the ratio CKC/number of mers of the oligonucleotide is from 0.001 to 0.5.

12. A medicament comprising an effective amount of at least one oligonucleotide and cetalkonium chloride (CKC), wherein the ratio of CKC to mers of the oligonucleotide is less than 0.55.

13. A pharmaceutical composition comprising an effective amount of at least one oligonucleotide, and cetalkonium chloride (CKC), in combination with one or more pharmaceutically acceptable excipients, wherein the ratio of CKC to mers of the oligonucleotide is less than 0.55.

14. The medicament according to claim 12, wherein the oligonucleotide is an antisense oligonucleotide directed against specific cellular receptors.

15. A method for the prevention, treatment or relief of eye, lung, and/or respiratory tract conditions, comprising administering the composition of claim 1 to a patient in need thereof.

16. The method according to claim 15, wherein the composition is administered directly or otherwise, to all or a portion of the alimentary canal, skin, eyes, pulmonary tract, respiratory tract, or to the mucosa, of an animal.

17. A method to enhance stability and/or improve penetration of nucleosidic moieties within targeted cells, comprising administering the composition of claim 1 to a patient in need thereof.

18. The pharmaceutical composition according to claim 13, wherein the oligonucleotide is an antisense oligonucleotide directed against specific cellular receptors.

* * * * *

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tggcacttta ggtggctg                                                    18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
actcatattc atagggtg                                                    18